United States Patent (10) Patent No.: US 8,940,740 B2
Pathak et al. (45) Date of Patent: Jan. 27, 2015

(54) SMALL MOLECULE INHIBITORS OF BACTERIAL MOTILITY AND A HIGH THROUGHPUT SCREENING ASSAY FOR THEIR IDENTIFICATION

(75) Inventors: Ashish K. Pathak, Birmingham, AL (US); Jorge A. Benitez, Atlanta, GA (US); Anisia J. Silva-Benitez, Atlanta, GA (US)

(73) Assignee: Southern Research Institute, Birmingham, AL (US)

( * ) Notice: Subject to any disclaimer, the term of this patent is extended or adjusted under 35 U.S.C. 154(b) by 577 days.

(21) Appl. No.: 13/284,609

(22) Filed: Oct. 28, 2011

(65) Prior Publication Data

US 2012/0108615 A1    May 3, 2012

Related U.S. Application Data

(60) Provisional application No. 61/407,695, filed on Oct. 28, 2010.

(51) Int. Cl.
| | | |
|---|---|---|
| A01N 43/58 | (2006.01) |
| A61K 31/50 | (2006.01) |
| A01N 43/54 | (2006.01) |
| C07D 239/42 | (2006.01) |
| C07D 401/04 | (2006.01) |
| C07D 471/04 | (2006.01) |
| C07D 471/22 | (2006.01) |
| C07D 487/04 | (2006.01) |
| A61K 31/505 | (2006.01) |
| A61K 31/5377 | (2006.01) |

(52) U.S. Cl.
CPC .................................. *A61K 31/5377* (2013.01)
USPC ............ 514/247; 514/256; 514/257; 514/269

(58) Field of Classification Search
USPC .................................. 514/247, 256, 257, 269
See application file for complete search history.

(56) References Cited

U.S. PATENT DOCUMENTS

2006/0025406 A1    2/2006  Zembower et al.
2008/0107691 A1    5/2008  Ravichandran et al.

OTHER PUBLICATIONS

International Preliminary Report on Patentability dated May 10, 2013 for PCT/US2011/058400.

*Primary Examiner* — Yong Chong
(74) *Attorney, Agent, or Firm* — Novak Druce Connolly Bove + Quigg LLP

(57) ABSTRACT

Certain compounds are provided that can selectively inhibit motile bacteria such as *V. cholerae* motility. These compounds can indirectly diminish production of cholera toxin and other major virulence required by the cholera bacterium to cause disease.

6 Claims, 8 Drawing Sheets

SMALL MOLECULE INHIBITORS OF BACTERIAL MOTILITY AND A HIGH THROUGHPUT SCREENING ASSAY FOR THEIR IDENTIFICATION

CROSS-REFERENCE TO RELATED APPLICATIONS

This application claims, priority under 35 USC 119 to U.S. provisional application Ser. No. 61/407,695, filed Oct. 28, 2010.

FEDERALLY SPONSORED RESEARCH AND DEVELOPMENT

This invention was supported in part by Grant AI 081039 from the National Institutes of Health and the U.S. Government has certain rights in the invention.

TECHNICAL FIELD

The present disclosure relates to inhibiting bacterial motility such as in the bacterium *Vibrio cholerae* to prevent it from establishing infection in the human body. The present disclosure also relates to disease prophylaxis to contain epidemic outbreaks such as cholera. By way of example, this disclosure relates to inhibitors of *V. cholerae* motility that indirectly diminish the expression of other virulent factors such as cholera toxin. The present disclosure also relates to novel compounds that inhibit bacterial motility.

BACKGROUND OF DISCLOSURE

Numerous bacterial pathogens, particularly those that colonize fast flow areas in the bladder and gastrointestinal (GI) tract, require motility to establish infection and subsequently spread within the initially colonized tissue. For instance, flagellum has been recognized as a major virulent factor in *Campylobacter jejuni*, which annually causes 2.5 million cases of diarrhea (Guerry 1994). In *Salmonella enteritidis* serovar Typhimurium, the interaction between released flagellin and Toll-like receptor 5 is a major component of the inflammatory response conducive to enteritis (Carlo and Podolsky 2003, McCormick 2003). In *V. cholerae*, motility is required for intestinal colonization and spreading of the infection along the GI tract (Lee et al. 2002, Silva et al. 2006).

Cholera is an acute water-borne diarrheal disease caused by *V. cholerae* of serogroups O1 and O139. Cholera continues to be a major public health concern in endemic areas of south Asia and Africa. The disease generally presents itself in the form of rapidly spreading outbreaks and is a common sequel of natural disasters such as hurricanes, tsunamis, flooding and earthquakes. In 2009, 221,226 laboratory-confirmed cholera cases and 4946 deaths were reported to the World Health Organization (WHO) (Cholera 2009). However, a more realistic estimate of the prevalence of cholera is 5.5 million cases and 130,000 deaths per year. The emergence of multiple antibiotic resistant *V. cholerae* O1 and O139 strains has been recognized as a major concern (Das et al. 2008, Mwansa et al. 2007, Okeke et al. 2007, Roychowdhury et al. 2008). Oral inactivated whole cell and live genetically-attenuated vaccines are currently under intense evaluation. Nevertheless, the capacity of these vaccines to contain rapidly spreading cholera outbreaks is under debate and their use for this purpose is not recommended by the WHO. Furthermore, the deployment of cholera vaccines in isolated regions still poses significant logistic challenges. The availability of new prophylactic and/or therapeutic agents is required to diminish the burden of cholera. The hallmark of *V. cholerae* strains that cause epidemic cholera is the production of two major virulence factors: cholera toxin and the toxin-coregulated pilus. Cholera toxin is responsible for the profuse watery diarrhea and the toxin-coregulated pilus is required for intestinal colonization (Finkelstein 1992, Kaper et al. 1995). Strains in which the genes encoding these virulence factors have been deleted are avirulent.

SUMMARY OF DISCLOSURE

The present disclosure relates to inhibiting motility of a motile bacteria by contacting the bacteria with a compound represented by the following formula A or their stereoisomerically pure forms, or a pharmaceutically acceptable salt thereof, a solvate thereof, a prodrug thereof, and mixtures thereof:

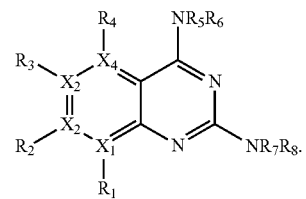

A

In formula A, atoms labeled $X_1$ thru $X_4$ are independently chosen from C or N. Whenever any of the $X_1$ to $X_4$=C, then those atoms may optionally and independently be substituted by the corresponding substituents $R_1$ to $R_4$, where each of the $R_1$ to $R_4$ is individually selected from the group consisting of hydrogen, substituted or unsubstituted alkyl including trifluoromethyl, substituted or unsubstituted aryl, substituted or unsubstituted arylalkyl, substituted or unsubstituted cycloalkyl, substituted or unsubstituted heterocyclic, substituted or unsubstituted heteroaryl, hydroxy, alkoxy, carbonyloxy, halogen, azido, cyano, nitro, alkylthio, carboxyl and corresponding esters, carboxamido and amino and mono- or disubstituted amino including amido and sulfonamido. Similarly, the substituents $R_5$, $R_6$, $R_7$ and $R_8$ are individually and independently selected from the group consisting of hydrogen, substituted or unsubstituted alkyl, substituted or unsubstituted aryl, substituted or unsubstituted arylalkyl, substituted or unsubstituted cycloalkyl, substituted or unsubstituted heterocyclic, substituted or unsubstituted heteroaryl, substituted carboxamido and substituted or unsubstituted sulfonamido.

The present disclosure also relates to treating a patient by inhibiting motility of a motile bacteria in a patient exposed to the bacteria which comprises administering to the patient an effective amount of at least one of the above compounds.

A further aspect of the present disclosure relates to prophylaxis treatment of disease outbreak due to motile bacteria by administering to a patient in danger of exposure to motile bacteria at least one of the above compounds.

Inhibitors of bacterial motility can be identified by a phenotype assay which comprises:
a) introducing a motile bacterial culture to wells in a multiwell device,
b) inoculating the motile bacteria with a compound being tested,
c) allowing the motile bacteria to spread through the well, d) determining the center reading of absorbance to determine the extent to which the motile bacteria spread across the well;

e) comparing the center reading to that for untreated motile bacteria;

f) contacting the motile bacteria inoculated with the compound being tested with alamarBlue to determine the viability of the inoculated motile bacteria.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

SUMMARY OF DRAWINGS

FIG. 6A-C demonstrate that Q24DA inhibits *V. cholerae* virulence gene expression.

FIG. 6A: In vitro virulence gene expression. Strain C7258 was grown in AKI medium (control) and the same medium containing Q24DA (10 μg/mL). CT and the TCP major subunit TcpA were determined by enzyme-linked immunosorbent assay and western blot, respectively Results are the mean of three independent cultures±standard deviation.

FIG. 6B: In vivo virulence gene expression. Three rabbit ileal loops were inoculated with pure CT (20 μg), strain C7258 (WT), C7258 containing 10 μg/mL Q24DA and C7258ΔmotY. Results were expressed as fluid accumulation (FA) in mL per cm of loop±standard deviation. Symbols *, significant p=0.026; **, significant p=0.029.

FIG. 6C, Expression of the ToxT regulator. Strain C7258 was grown as in FIG. 6A in the absence (control) and presence (treated) of Q24DA and the expression of toxT measured by qRT-PCR using recA mRNA as reference. Results are the mean of three independent cultures±standard deviation.

BEST AND VARIOUS MODES

Figure 1:
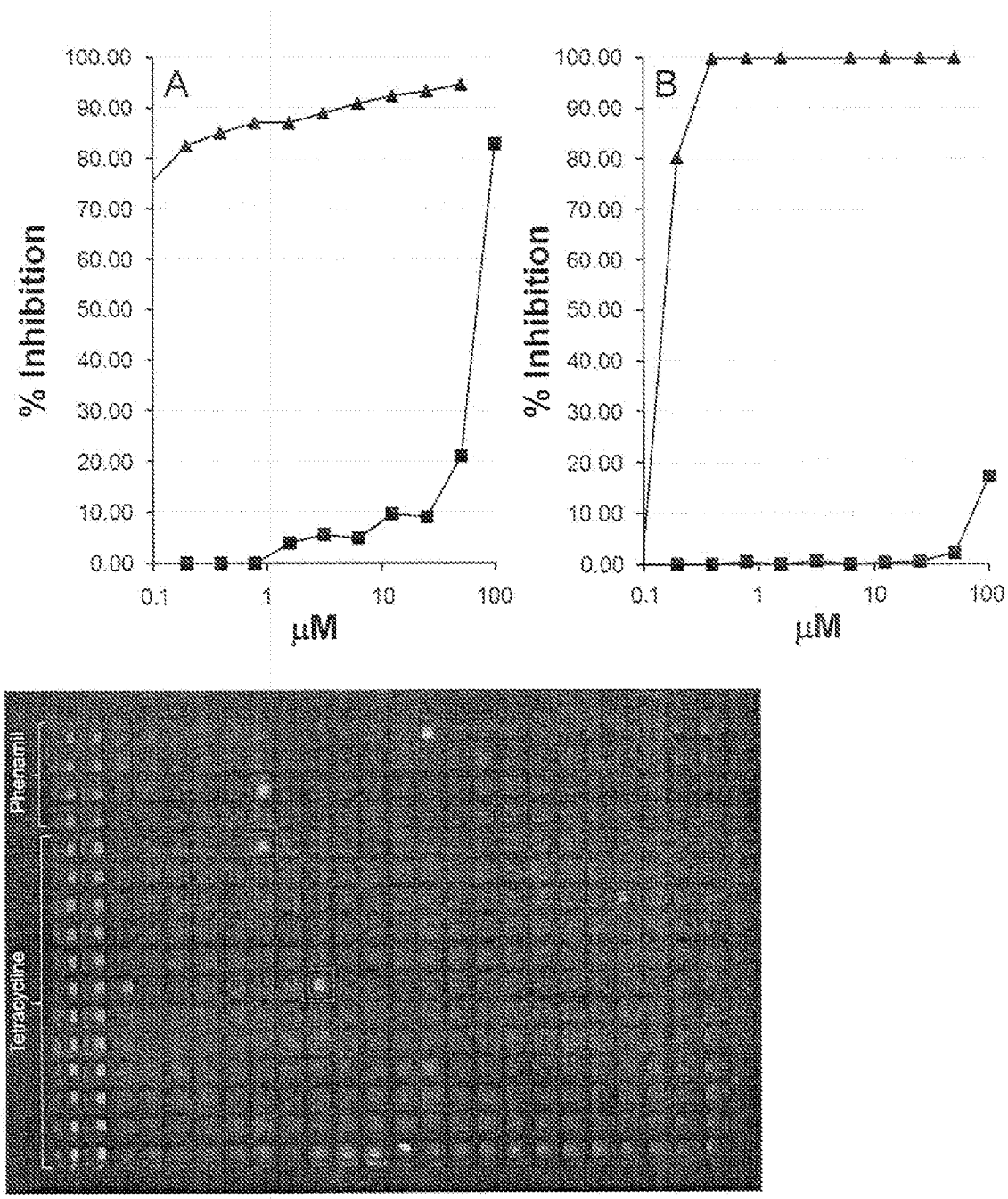
FIG. 1. The Top panels are graphs showing the dose response evaluations of motility inhibitor phenamil (■) and bactericidal compound tetracycline (▲) in 384-well plates for motility inhibition measured by the absorbance reading (panel A), and for toxicity (bactericidal activity) measured with alamarBlue. The Bottom panel shows a 384-well sample plate from pilot screening. Plates were inoculated with the motile strain C7258. Columns 1-2 contain phenamil (rows 1-4) or tetracycline (rows 5-16). Compounds that specifically inhibit motility (phenamil-like) can be distinguished from those with bactericidal activity (Tet-like) in this plate. For instance, compounds like phenamil that only inhibit motility yield a bright (pink) alamarBlue signal; compounds that do not affect motility or viability, yield a blurred alamarBlue signal due to bacterial spreading across the well; bactericidal compounds yield a Tet-like (blue) alamarBlue signal.
Figure 2:
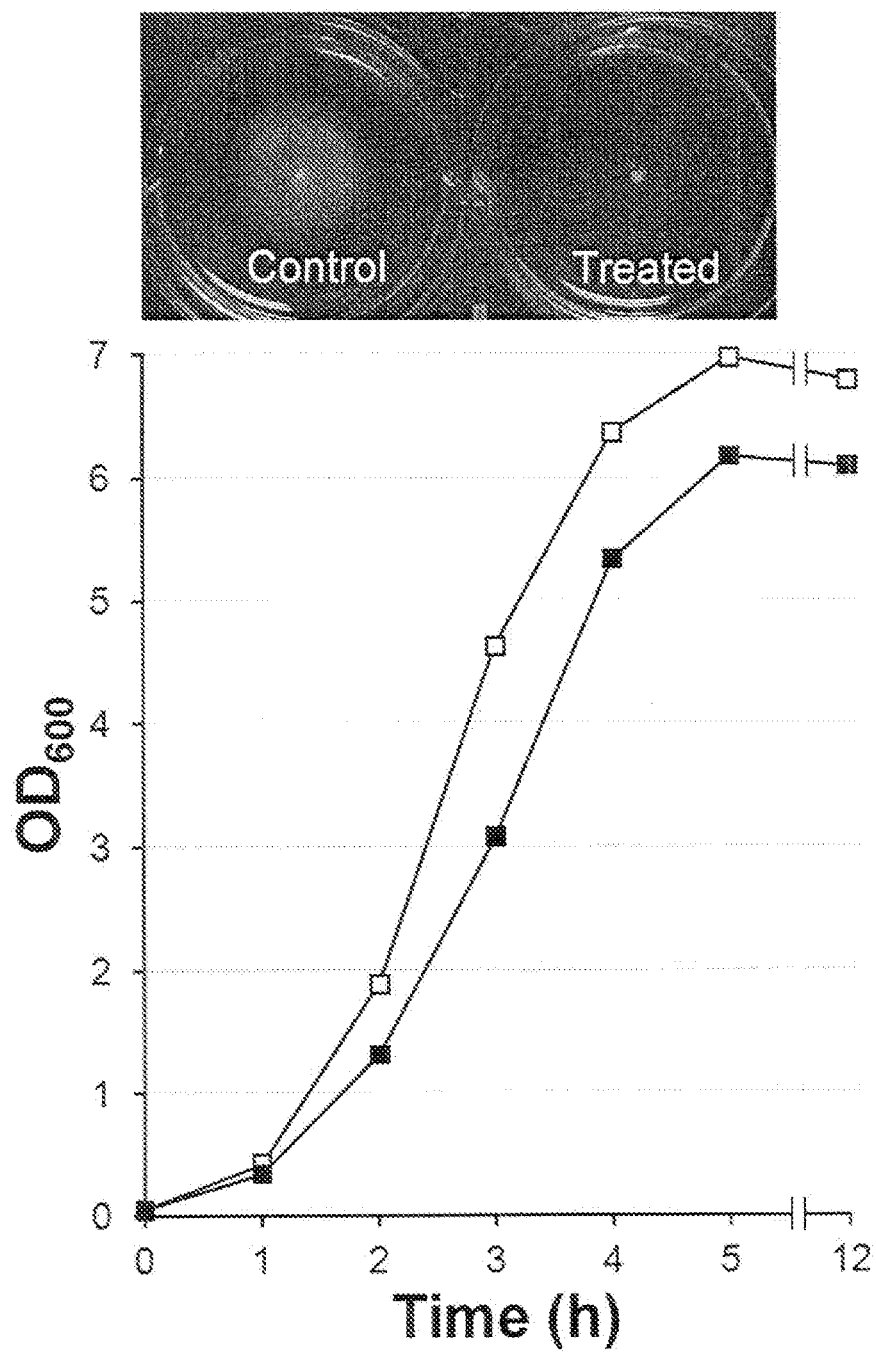
FIG. 2 is a graph illustrating the effect of quinazoline-2,4-diamino analog (Q24DA) on motility and growth rate. The Top panel is a confirmation of motility inhibition by Q24DA in swarm agar stabbed with a saturated culture of the El Tor biotype strain C7258. The Bottom panel shows the growth curve of strain C7258 in LB medium pH 7.4 in the absence (□) and presence (■) of compound Q24DA (10 μg/mL)
Figure 3:
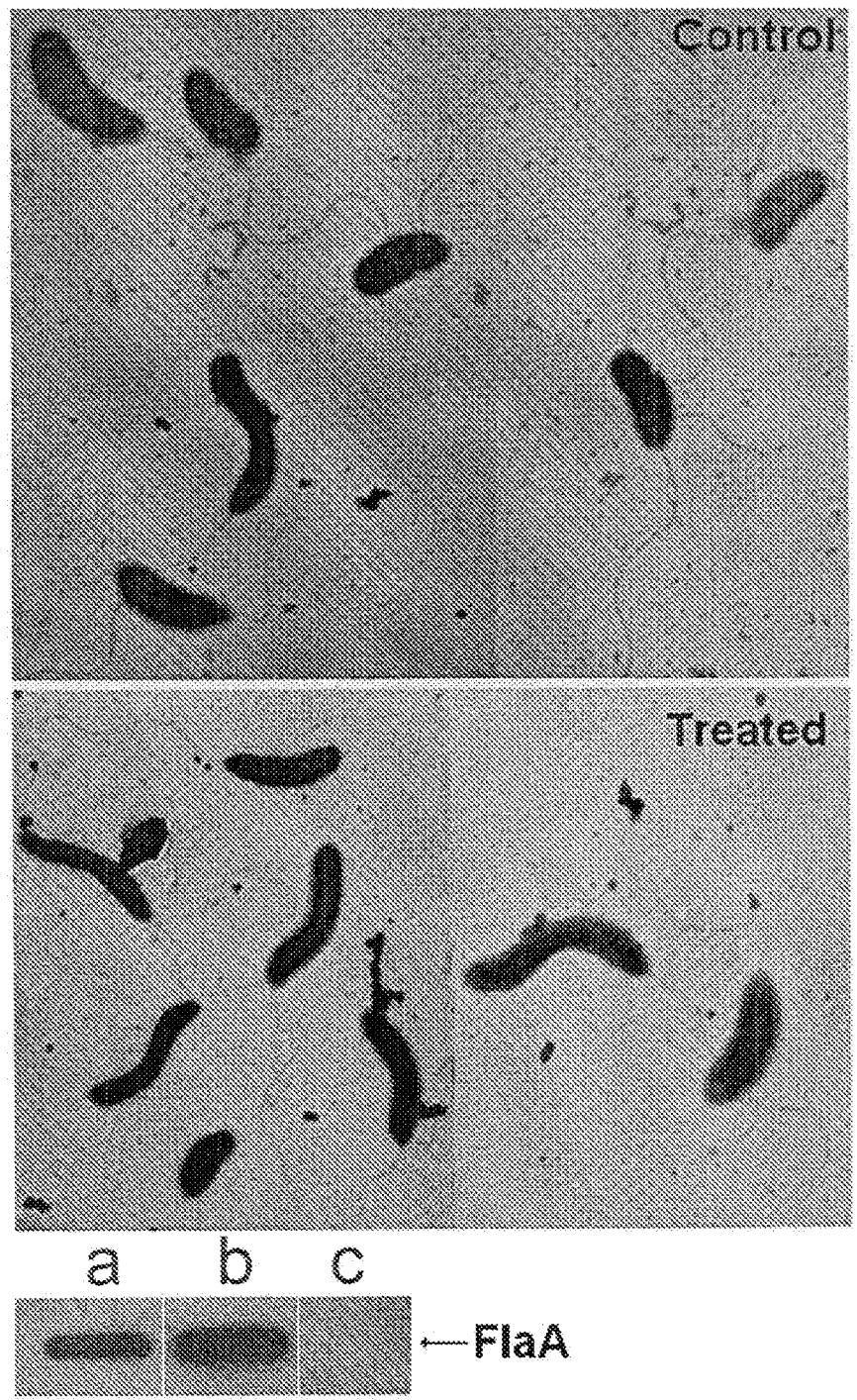
FIG. 3 illustrates the flagellin expression in the presence of Q24DA. In the Top panel strain C7258 was grown in LB medium in the absence (control) and presence (treated) of compound Q24DA and the cells were examined by transmission electron microscopy for the expression and assembly of a wild type flagellum. In the Bottom panel, Cell pellets and supernatants of strain C7258 grown as indicated above were analyzed by western blot for core flagellin A expression using a monoclonal antibody raised against pure FlaA protein. Lane a, control (untreated) culture; lane b, culture containing Q24DA; lane c, culture of core flagellin-deficient mutant.
Figure 4:
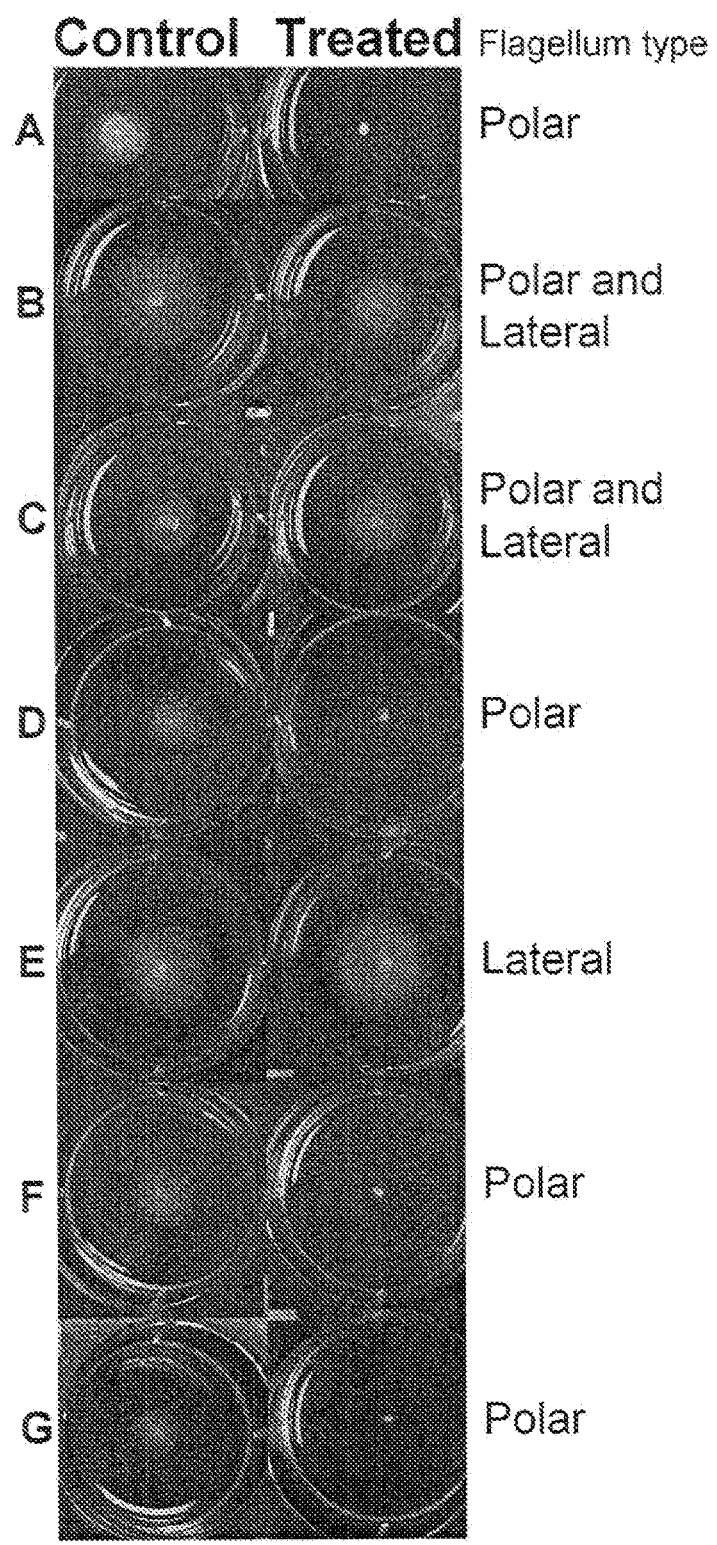
FIG. 4 shows the effect of compound Q24DA on a *V. cholerae* strains of the classical biotype and other pathogenic Vibrios. *V. cholerae* and *V. vulnificus* make a single polar flagellum (Fla) powered by sodium motive force (SMF). *V. parahemolyticus* makes a polar flagellum powered by SMF and a lateral flagellum (Laf) powered by proton motive force Swarm agar plates were stabbed with saturated cultures of different pathogenic Vibrios to show that Q24DA is specific for the polar flagellum powered by SMF. (A) *V. cholerae* 0395; (B) *V. parahaemolyticus* B22 (Fla+ Laf+); (C) *V. parahaemolyticus* LM5674 (Fla+ Laf+); (D) *V. parahaemolyticus* LM1017 (Fla+ Laf−); (E) *V. parahaemolyticus* LM5392 (Fla− Laf+); (F) *V. parahaemolyticus* 7890 (Fla+ Laf−); (G) *V. vulnificus* LAM624.
Figure 5:
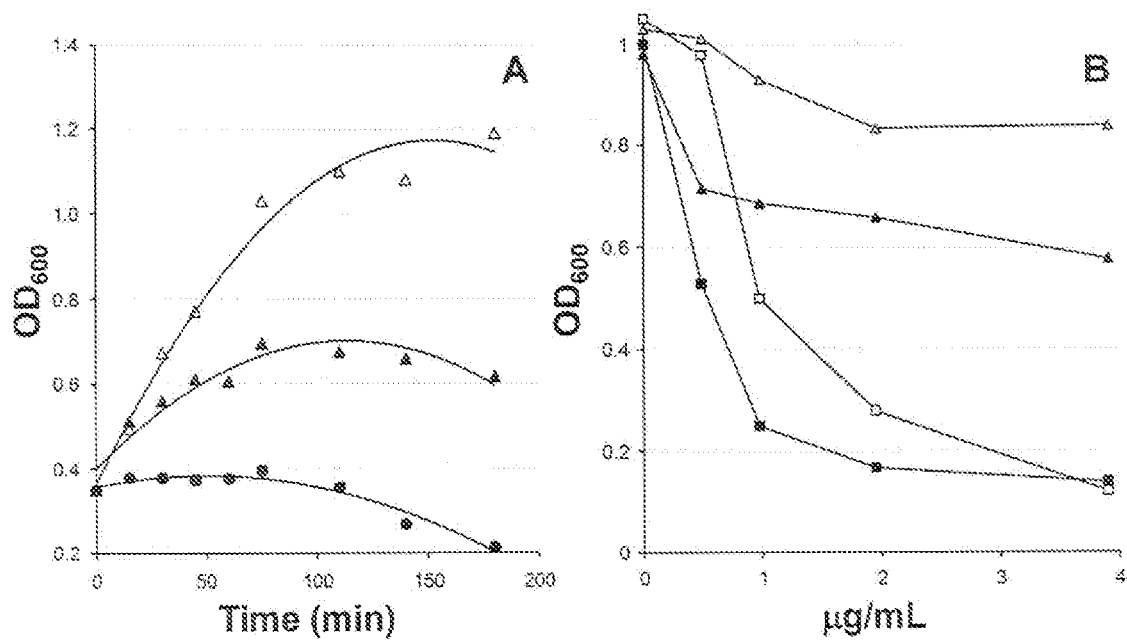
FIG. 5 shows the phenotypic effects of compound Q24DA linked to Na+ bioenergetics. Panel A: Q24DA enhances the inhibitory effect of blocking the PMF. Strain C7258 was grown in LB medium pH 8.6 containing 0.3 M NaCl. At OD600 0.35, carbonylcyanide m-chlorophenylhydrazone (CCCP) (5 μM) was added to inhibit PMF. Symbols: (Δ), control; (▲), medium containing Q24DA (10 μg/mL); (●) medium containing 2-n-heptyl-4-hydroxyquinoline-N-oxide (HQNO) (5 μM). Panel B: Effect of Q24DA on *V. cholerae* sensitivity to fluoroquinolones. Strain C7258 was grown in LB medium in 96-well microtiter plates containing different concentrations of norfloxacin and ciprofloxacin. Plates were incubated at 37° C. for 16 h and growth measured by reading the OD600. Symbols: (Δ), norfloxacin; (▲) norfloxacin and Q24DA; (□), ciprofloxacin; (■) ciprofloxacin and Q24DA.
Figure 6A:
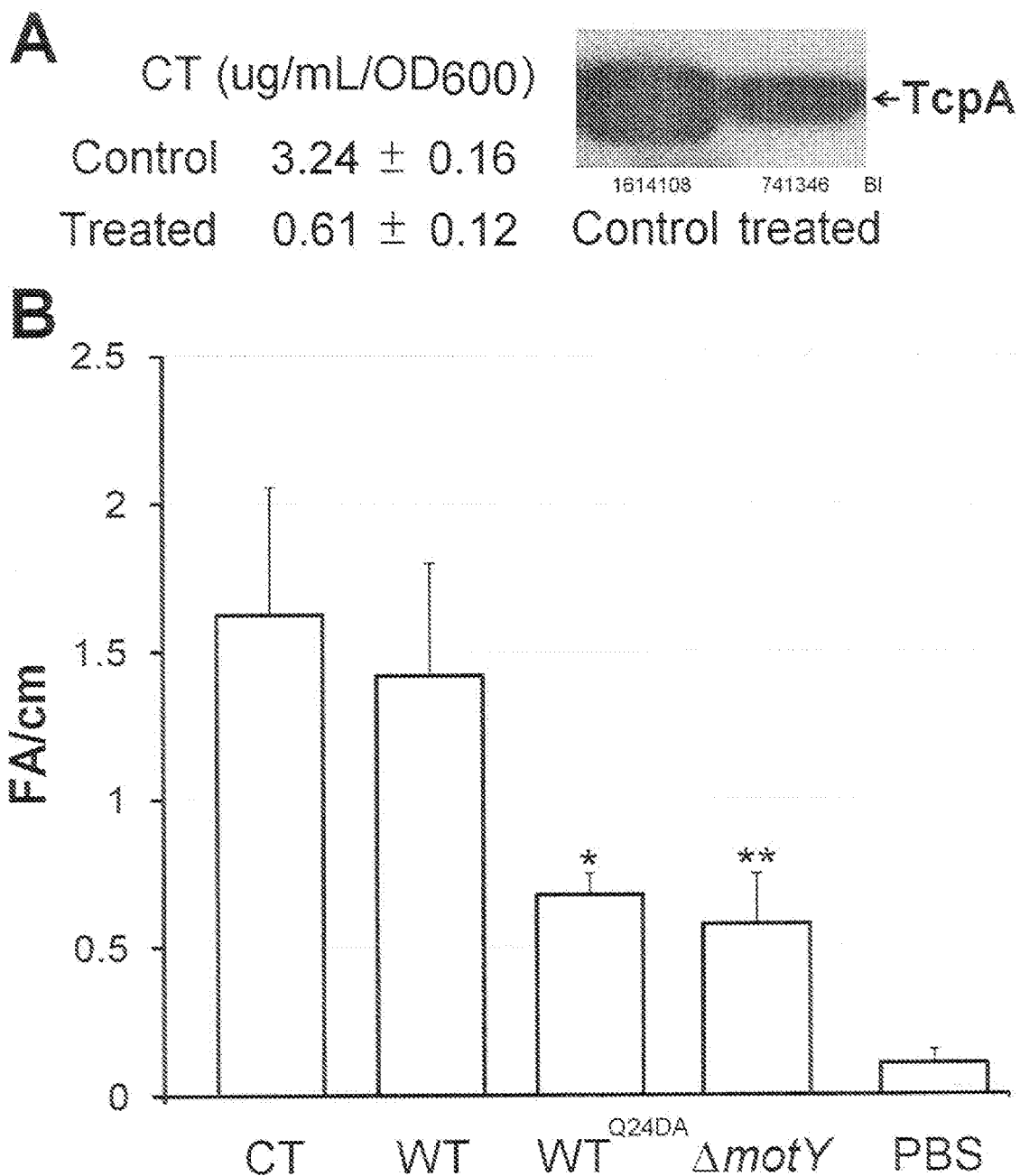
Figure 6C:
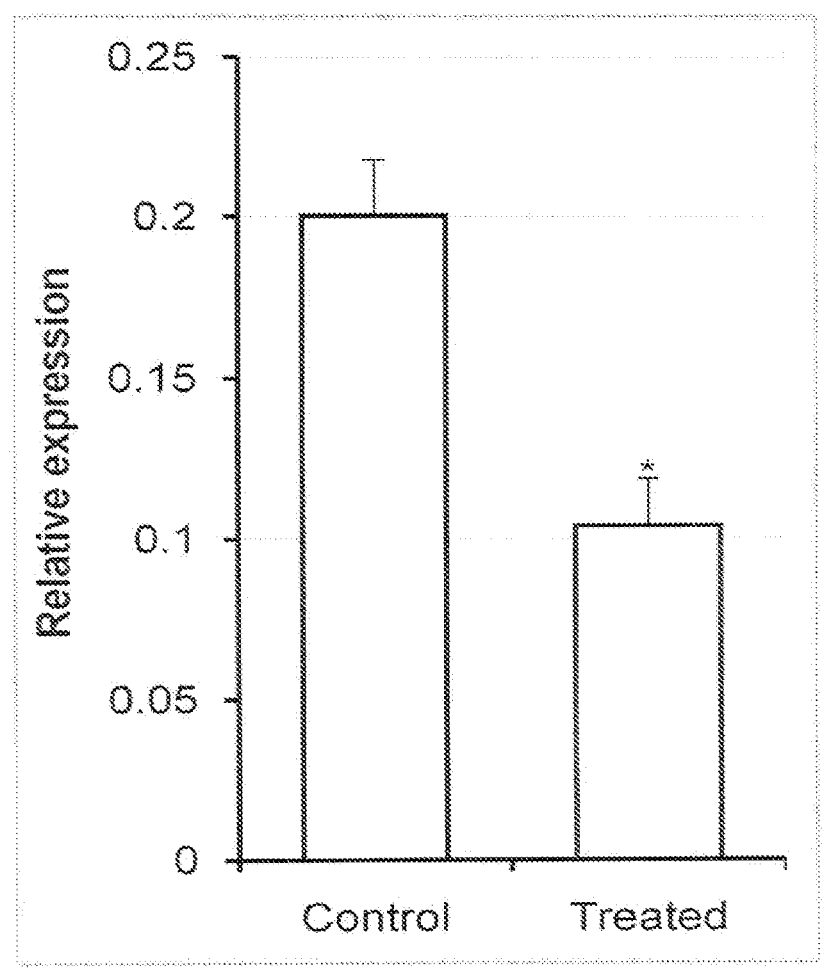
Figure 7:
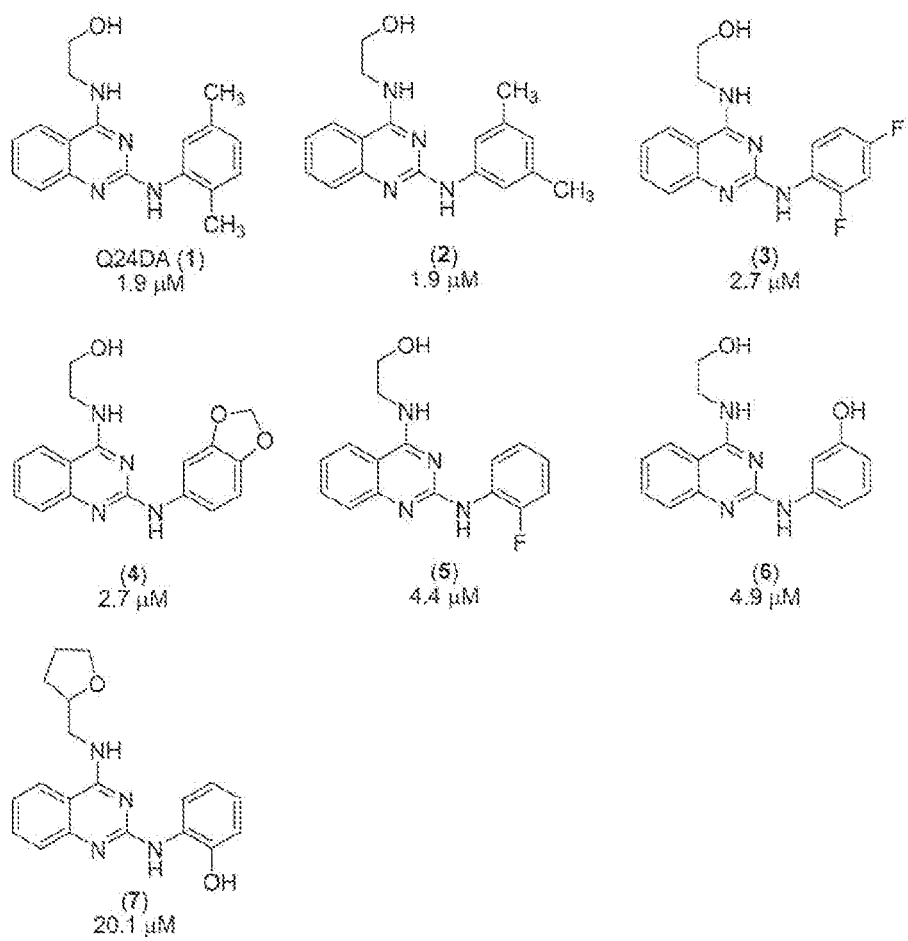
FIG. 7 shows inhibition (IC$_{50}$) of motility by chemical analogs of Q24DA. A. The IC$_{50}$ values were determined by measuring the swarm diameter produced by three independent cultures of strain C7258 stabbed in swarm agar supplemented with twofold dilutions of each compound (numbered 1 through 7) starting at 10 μg/mL. B. Swarm agar test and growth in broth. Overnight cultures of strain C7258 containing >10$^9$ cells/mL were stabbed in 4 mL of soft agar containing 10 μg/mL of compounds 2-7. In parallel, three overnight cultures of strain C7258 were diluted 1:100 in LB broth containing the above concentration of compounds 2-7 in 96-well microtiter plates. Plates were incubated at 16 hours at 30° C.
Figure 7:
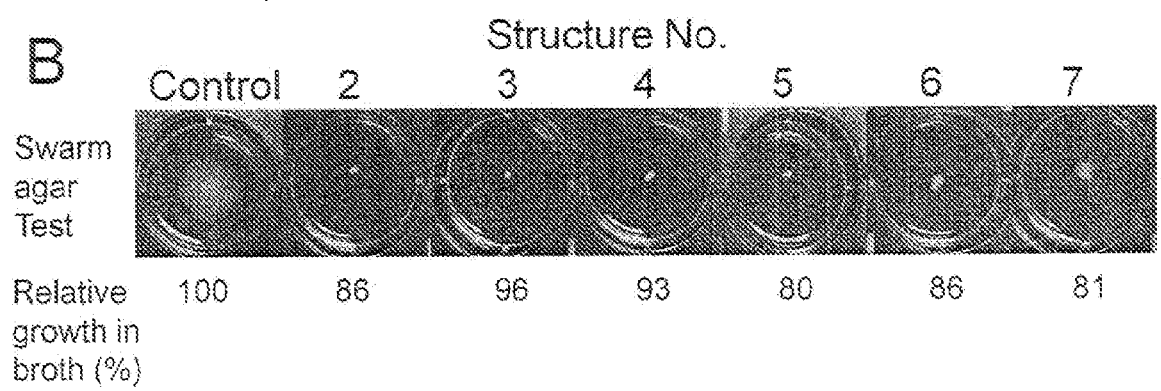

The compounds employed in the present disclosure are represented by the following formula A or their stereoisomerically pure forms, or a pharmaceutically acceptable salt thereof, a solvate thereof, a prodrug thereof, and mixtures thereof:

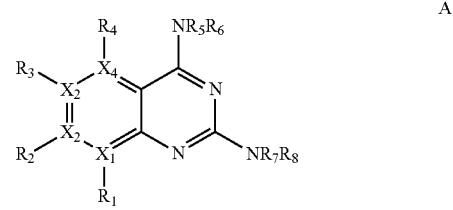

A

In formula A, atoms labeled $X_1$ thru $X_4$ are independently chosen from C or N. Whenever any of the $X_1$ to $X_4$=C, then those atoms may optionally and independently be substituted by the corresponding substituents $R_1$ to $R_4$, where each of the $R_1$ to $R_4$ is individually selected from the group consisting of hydrogen, substituted or unsubstituted alkyl including trifluoromethyl, substituted or unsubstituted aryl, substituted or unsubstituted arylalkyl, substituted or unsubstituted cycloalkyl, substituted or unsubstituted heterocyclic, substituted or unsubstituted heteroaryl, hydroxy, alkoxy, carbonyloxy, halogen, azido, cyano, nitro, alkylthio, carboxyl and corresponding esters, carboxamido and amino and mono- or disubstituted amino including amido and sulfonamido. Similarly, the substituents $R_5$, $R_6$, $R_7$ and $R_8$ are individually and independently selected from the group consisting of hydrogen, substituted or unsubstituted alkyl, substituted or unsubstituted aryl, substituted or unsubstituted arylalkyl, substituted or unsubstituted cycloalkyl, substituted or unsubstituted heterocyclic, substituted or unsubstituted heteroaryl, substituted carboxamido and substituted or unsubstituted sulfonamido.

Listed below are definitions of various terms used to describe this disclosure. These definitions apply to the terms as they are used throughout this specification, unless otherwise limited in specific instances, either individually or as part of a larger group. Also, in the formulae described and claimed herein, it is intended that when any symbol appears more than once in a particular formula or substituent, its meaning in each instance is independent of the other.

"Effective amount" refers to an amount of a compound as described herein that may be therapeutically effective to treat a viral infection or inhibit a virus. The precise amount of these compounds required will vary with the particular compounds or derivatives employed, the age and condition of the subject to be treated, and the nature and severity of the condition. However, the effective amount may be determined by one of ordinary skill in the art once aware of this disclosure without undue experimentation.

The phrase "patient in danger of exposure to motile bacteria" refers to individuals exposed to conditions in locations in which such events as "hurricanes, tsunamis, floods and earthquakes" have occurred wherein a there is a propensity of an epidemic outbreak occurring.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids.

Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

A "Prodrug" is a compound that is converted within the body into its active form that has a medical effect. Prodrugs may be useful when the active drug may be too toxic to administer systemically, the active drug is absorbed poorly by the digestive tract, or the body breaks down the active drug before it reaches its target. Methods of making prodrugs are disclosed in Hans Bundgaard, Design of Prodrugs (Elsevier Science Publishers B.V. 1985), which is incorporated herein by reference in its entirety.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined above.

Carboxamides, —NHC(O)R

Carbamates, —NHC(O)OR (Acyloxy)alkyl Carbamates, NHC(O)OROC(O)R

Enamines, —NHCR(=CHCRO$_2$R) or —NHCR(=CH-CRONR$_2$)

Schiff Bases, —N=CR$_2$

Mannich Bases (from carboximide compounds), RCONHCH$_2$NR$_2$

Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the disclosure include esters (—CO$_2$R) where the R group corresponds to any alcohol whose release in the body through enzymatic or hydrolytic processes would be at pharmaceutically acceptable levels.

Another prodrug derived from a carboxylic acid form of the disclosure may be a quaternary salt type

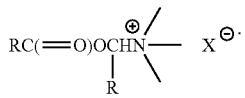

of structure described by Bodor et al., J. Med. Chem. 1980, 23, 469.

It is of course understood that the compounds of the present disclosure relate to all optical isomers and stereo-isomers at the various possible atoms of the molecule.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted. The aromatic or aryl groups are more typically phenyl and alkyl substituted aromatic groups (aralkyl) such as phenyl $C_{1-3}$ alkyl and benzyl.

The term "aralkyl" or "arylalkyl" refers to an aryl group bonded directly through an alkyl group, such as benzyl or phenethyl.

The term "substituted aryl" or "substituted alkylaryl" refers to an aryl group or alkylaryl group substituted by, for example, one to four substituents such as aryl, substituted aryl, heterocycle, substituted heterocycle, alkyl; substituted alkyl, halo, trifluoromethoxy, trifluoromethyl, hydroxy, alkoxy, azido, cycloalkyloxy, heterocyclooxy, alkanoyl, alkanoyloxy, amino, alkylamino, aralkylamino, hydroxyalkyl, aminoalkyl, azidoalkyl, alkenyl, alkynyl, allenyl, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl. "Substituted benzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl and adamantyl. Exemplary substituents include one or more alkyl groups as described above, or one or more groups described above as alkyl substituents.

The term "alkyl" refers to straight or branched chain unsubstituted hydrocarbon groups of 1 to 20 carbon atoms, and more typically 1 to 8 carbon atoms and even more typically unsubstituted alkyl groups of 1 to 4 carbon atoms. Examples of suitable alkyl groups include methyl, ethyl and propyl. Examples of branched alkyl groups include isopropyl and t-butyl.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom. Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, isopyrrole, 1,2, 3-triazole, 1,2,4-triazole, oxazole, thiazole, pyrimidine, aziridines, thiazole, 1,2,3-oxadiazole, thiazine, pyrrolidine, oxaziranes, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl-, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkylpyrimidines, N5-benzylpyrimidines, N5-halopyrimidines, N5-vinyl-pyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituents selected from hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "amino" as used herein refers to the group —NH$_2$.

Suitable monoalkylamino groups contain 1-6 carbon atoms and include monomethylamino, monoethylamino, mono-isopropylamino, mono-n-propylamino, mono-isobutyl-amino, mono-n-butylamino and mono-n-hexylamino. The alkyl moiety can be straight or branched chain.

Suitable dialkylamino groups contain 1-6 carbon atoms in each alkyl group. The alkyl groups can be the same or different and can be straight or branched chain. Examples of some suitable groups are dimethylamino, diethylamino, ethylmethylamino, dipropylamino, dibutylamino, dipentylamino, dihexylamino, methylpentylamino, ethylpropylamino and ethylhexylamino.

The term "carboxylate ester" (e.g., carboxylic acid ester) refers to a carboxy group —C(=O)OR', wherein R' is substituted or unsubstituted alkyl, substituted or unsubstituted alkenyl, substituted or unsubstituted alkynyl, substituted or unsubstituted carbocyclic, substituted or unsubstituted heterocyclic, substituted or unsubstituted aryl, or substituted or unsubstituted aralkyl.

When any of the above groups are substitutes, unless stated otherwise, they are typically substituted with at least one member selected from the group consisting of alkyl, hydroxyl, amino, halo and halogenated alkyl and more typically a fluoroalkyl such as trifluoromethyl.

The term "comprising" (and its grammatical variations) as used herein is used in the inclusive sense of "having" or "including" and not in the exclusive sense of "consisting only of." The term "a" and "the" as used herein are understood to encompass the plural as well as the singular.

Representative compounds according to the present disclosure along with test data are disclosed in the following Table 1:

TABLE-1

| | Motility data on Q24DA and related structures | | | |
| --- | --- | --- | --- | --- |
| ID's | Structure | THP-cell Toxicity* | Inhibition IC50* | Motility OD IC50* |
| AB00343282 | 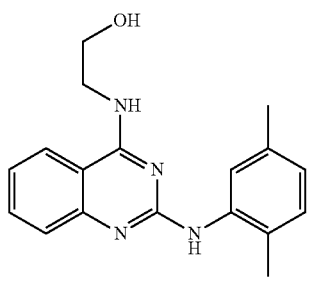 [SMILES: Cc1ccc(C)c(Nc2nc(NCCO)c3ccccc3n2)c1] Q24DA | — | 25.67 | 8.76 |
| 27296 | 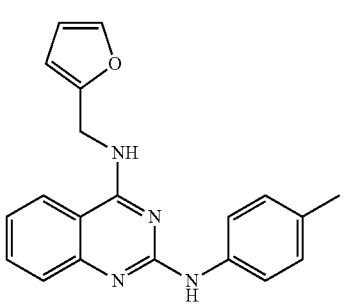 [SMILES: Cc1ccc(Nc2nc(NCc3ccco3)c3ccccc3n2)cc1] | 11.86 | 11.07 | 3.77 |
| 27299 | 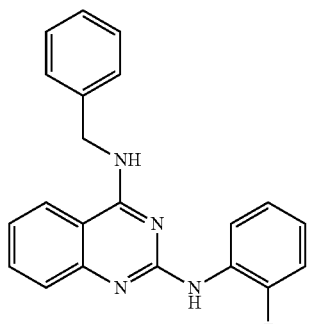 | 9.93 | 99.99 | 6.37 |

TABLE-1-continued
Motility data on Q24DA and related structures
| ID's | Structure | THP-cell Toxicity* | Inhibition IC50* | Motility OD IC50* |
|------|-----------|--------------------|--------------------|--------------------|
| 27307 | 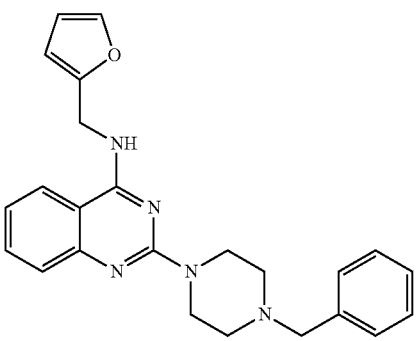 [SMILES: c1ccc(CN2CCN(c3nc(NCc4ccco4)c4ccccc4n3)CC2)cc1] | >40.00 | 37.89 | 34.86 |
| 27297 | 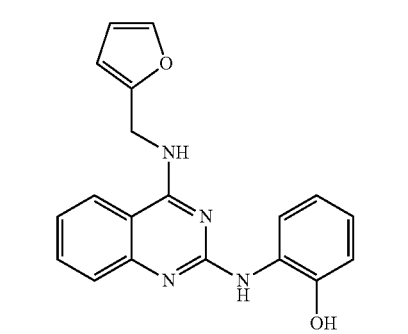 | 24.94 | 81.88 | 37.83 |
| 27301 | 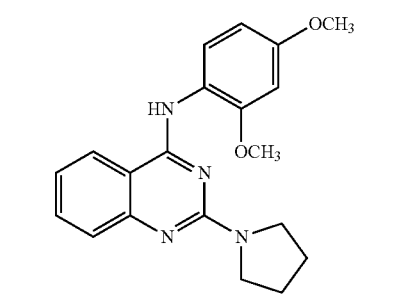 [SMILES: COc1ccc(Nc2nc(N3CCCC3)nc3ccccc23)c(OC)c1] | 18.84 | 81.97 | 46.62 |
| 27310 | 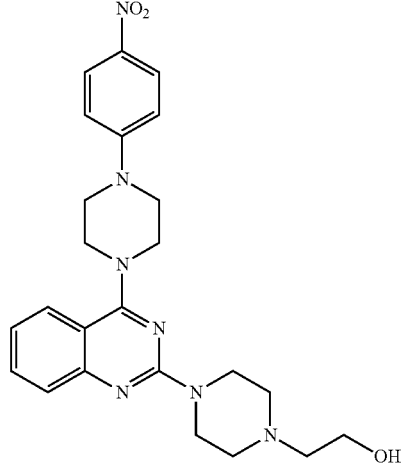 [SMILES: O=[N+]([O-])c1ccc(N2CCN(c3nc(N4CCN(CCO)CC4)nc4ccccc34)CC2)cc1] | 32.81 | 55.40 | 77.23 |

TABLE-1-continued

Motility data on Q24DA and related structures

| ID's | Structure | THP-cell Toxicity* | Inhibition IC50* | Motility OD IC50* |
|---|---|---|---|---|
| 27284 | 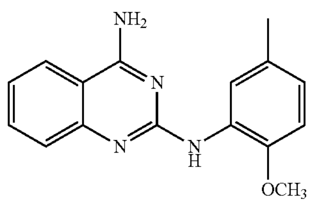 [SMILES: COc1ccc(C)cc1Nc1nc(N)c2ccccc2n1] | 30.33 | >100.00 | 81.25 |
| 27928 | 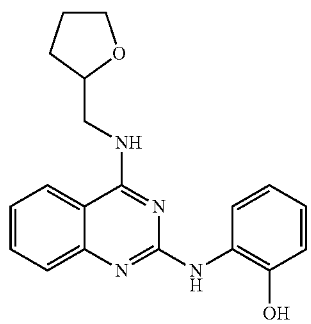 [SMILES: Oc1ccccc1Nc1nc(NCC2CCCO2)c2ccccc2n1] | 6.89 | 19.37 | 16.48 |
| 27916 | 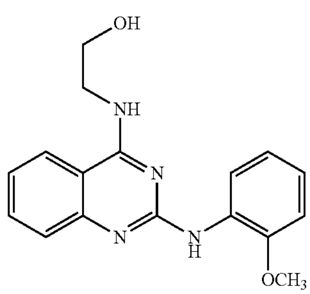 [SMILES: COc1ccccc1Nc1nc(NCCO)c2ccccc2n1] | 12.24 | 38.15 | 49.45 |
| 27910 | 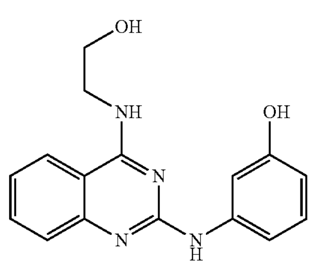 [SMILES: OCCNc1nc(Nc2cccc(O)c2)nc2ccccc12] | 1.19 | 46.99 | 22.17 |
| 27912 | 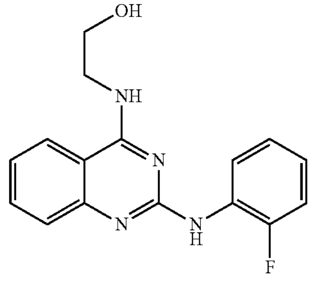 [SMILES: OCCNc1nc(Nc2ccccc2F)nc2ccccc12] | 1.71 | 14.43 | 4.89 |

TABLE-1-continued
Motility data on Q24DA and related structures
| ID's | Structure | THP-cell Toxicity* | Inhibition IC50* | Motility OD IC50* |
|---|---|---|---|---|
| 27908 | 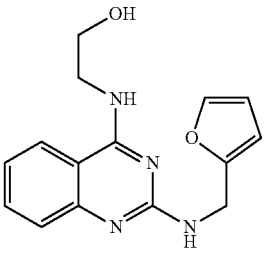 [SMILES: OCCNc1nc(NCc2ccco2)nc2ccccc12] | 13.77 | >100.00 | 45.63 |
| 27911 | 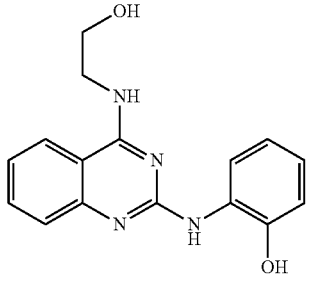 [SMILES: OCCNc1nc(Nc2ccccc2O)nc2ccccc12] | 12.79 | 34.25 | 29.54 |
| 27914 | 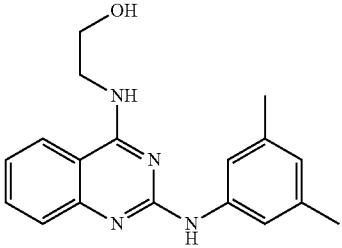 [SMILES: Cc1cc(C)cc(Nc2nc(NCCO)c3ccccc3n2)c1] | 1.87 | 10.06 | 6.96 |
| 27915 | 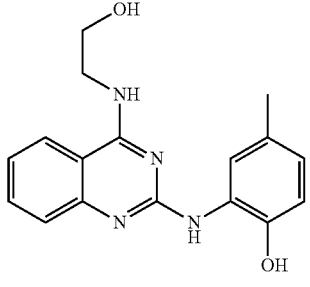 | 7.91 | 23.04 | 29.86 |
| 27917 | 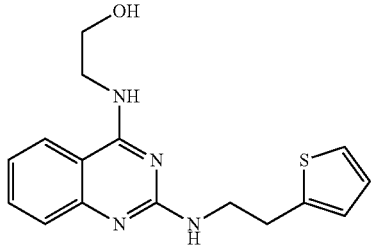 [SMILES: OCCNc1nc(NCCc2cccs2)nc2ccccc12] | 2.91 | 27.02 | 19.72 |

TABLE-1-continued

Motility data on Q24DA and related structures

| ID's | Structure | THP-cell Toxicity* | Inhibition IC50* | Motility OD IC50* |
|---|---|---|---|---|
| 27918 | [structure: 4-(2-hydroxyethylamino)-2-(2,4-dimethylphenylamino)quinazoline] | 2.11 | 15.55 | 6.10 |
| 27919 | [structure: 4-(2-hydroxyethylamino)-2-(benzo[d][1,3]dioxol-5-ylamino)quinazoline] | 1.42 | 29.79 | 10.78 |
| 27926 | [structure: 4-((tetrahydrofuran-2-yl)methylamino)-2-(furan-2-ylmethylamino)quinazoline] | 5.41 | 35.61 | 24.72 |
| 27929 | [structure: 4-((tetrahydrofuran-2-yl)methylamino)-2-(3,5-dimethylphenylamino)quinazoline] | 1.15 | 6.11 | 6.89 |
| 27930 | [structure: 4-((tetrahydrofuran-2-yl)methylamino)-2-(3-trifluoromethylphenylamino)quinazoline] | 4.20 | 81.20 | 7.59 |

*THP-cell Toxicity refers to toxicity of compounds to mammalian cells. Inhibition IC50 refers to toxicity of compound to bacteria as measured by alamarBlue. Motility OD IC50 refers to inhibition of bacterial motility as measured by the optical density reading made off-site with regard to the inoculation point. In this assay, best compounds would be those exhibiting the highest IC50s for the first two measures and lowest IC50 for the motility OD.

Experimental Protocol

Bacterial pathogens that colonize mucosal surfaces in the small intestine and bladder are constantly washed with fast flowing fluids. Examples of pathogens colonizing these sites are enterotoxigenic *E. coli* (ETEC), uropathogenic *E. coli* (UPEC), *Salmonella* sp. and *Vibrio cholerae*. In these cases the expression of motility can allow bacteria to move toward mucosal tissue and avoid clearance. It is also noteworthy that the flagellin released by many Gram-negative motile pathogens can be a significant contributor to inflammation. Finally, in many cases the expression of motility is mechanistically linked to the formation of antibiotic resistant biofilms. *V. cholerae*, the causative agent of cholera, is used herein as an example in which the method to identify inhibitors of motility can be applied to inhibit bacterial infection. The present disclosure relates to an improved phenotypic assay for inhibitors of bacterial motility based on off-center inoculation of a bacterial culture to wells containing soft agar, an incubation period allowing motile bacteria to spread throughout the well and center reading of absorbance ($OD_{615}$) to estimate the extent to which motile bacteria spread across the well (Malapaka et al. 2007). The assay has been fully automated, miniaturized to a 384-well format and combines an $OD_{615}$ reading with detection of viability using alamarBlue. To adapt the assay to 384-well format, the inoculation site needed to be out of the field of view for the $OD_{615}$ reading. This was accomplished by inoculating the plate in the top left corner of the well and reading the $OD_{615}$ to the right and down from well center. The procedure was standardized using defined *V. cholerae* mutants derived from the Wild type El Tor strain C7258, a clinical isolate from the 1991 Peru outbreak. In contrast to the motile strain C7258, colonies of non-motile mutant (C7258ΔmotY) did not interfere with the $OD_{615}$ even after 48 h of incubation. Initially, a Biomek FX was used to inoculate the plate using standard p30 pipette tips and a custom pipetting template that allowed the tips to be offset to the top left corner of the well and controlled the depth that the tip penetrated into the soft agar. The tips were immersed in a bacterial culture, tip touched to remove excess solution and inserted into the agar. The read location in the well was set using the plate dimension calibration on a Perkin Elmer Envision to be slightly off center to the bottom right to avoid interference from bacterial growth at the inoculation site. Using this method of inoculation the number of bacteria added to each well could not be controlled; some wells received a surplus of bacteria and some did not receive any. The amount of bacteria delivered to each well was dependent on the drops remaining on the outside of each pipette tip. Subsequently, an Echo 555 was used to deliver 2.5 ηL of bacterial culture to each well. Titration of the amount of bacteria showed that delivery of 10 bacteria/well produced reliable results. In order to differentiate between compounds that blocked motility and compounds that were toxic to the bacteria a readout using alamarBlue was added to the protocol. Using this method, a bactericidal compound such as tetracycline could be differentiated from a motility inhibitor compound such as phenamil (McCarter 2001). The inhibitory effect on motility of phenamil can be seen at 100 μM but had little effect on viability when measured with alamarBlue. In contrast, tetracycline killed the bacteria and while they would appear non-motile by the $OD_{615}$ reading, the alamarBlue reading shows that they are non-viable. Concurrently, DMSO was shown to have no effect on either readout at concentrations up to 1%. The final stage of HTS validation was to run a pilot screen of ~8,000 compounds with a repeat run on a second day. This procedure identifies any automation issues that are not obvious when handling two or three plates. Pearson's correlations were moderate (0.52 for $OD_{615}$ and 0.56 for alamarBlue) for both readouts and between plate and day-to-day assay variations were minimal. A summary of the assay protocol is provided below:

| Protocol summary | |
|---|---|
| Plate | 384 well black clear bottom containing 50 μl LB media with 0.3% agar. |
| Compounds | 0.3% soft agar plates are prepared in advance and stored at 4° C. for up to a month dispensed with Echo 550 to top of soft agar and allowed to diffuse for 2-4 hours at room temp pilot screen conducted at 10 μg/ml |
| Inoculation | 10 bacteria in 2.5 nl dispensed with an Echo 555 into bottom left corner of well |
| Incubation | 30° C., 16-24 hours high humidity |
| Read Motility | $OD_{615}$-offset above and to the right of center-diagonal-to inoculation site; Envision |
| Addition | 5 μl of 100% AlamarBlue with Wellmate |
| Incubation | 30° C. 1-1.5 hour, high humidity |
| Read Toxicity | Fl top read ex535, em595 after addition of AlamarBlue; Envision |
| Assay statistics | |
| Validation | Z values: 0.6 to 0.8 signal to noise: 173 signal to background: 7 Dose response to Phenamil: (motility) and Tetracycline (Toxicity) |
| Pilot Screen | 8,093 compounds were screened in duplicate on two different days |
| Z | Ave-0.70, Min-0.5, Max-0.81 |
| Bacteria control-DMSO | Ave-0.73 OD615, CV-5.6 |
| Viability control-Tetracycline | Ave-0.10 OD615, CV-3.6 |
| Motility control-Phenamil | Ave-0.10 OD615, CV-3.2 |
| Hit rate | 0.20% |

Ten compounds were identified from the pilot screen that appeared to inhibit motility. These compounds were screened in dose response. Four compounds were identified that inhibited motility and showed no toxicity; $IC_{50}$ values were 1.9-14 μg/ml. Six compounds were identified that inhibited motility with $IC_{50}$ values in the 1.9-11 μg/ml range but showed toxicity at the high test concentration. These compounds behaved similar to phenamil. In summary, the soft agar swarm assay has been used historically to evaluate motility, but has not been amenable to HTS. By adapting this soft agar assay to 384-well format it is now practical to conduct large scale screening campaigns to identify inhibitors of bacterial motility. Measuring motility by reading $OD_{615}$ followed by viability with alamarBlue, allows differentiation of bactericidal compounds from true motility inhibitors in a single screen.

A group of compounds were selected for secondary assays and followup studies. The concentration of cells used in our HTS assay was chosen to be low in order to maximize the initial hit rate. Five inhibitors were tested in swarm agar plates stabbed with saturated cultures of strain C7258. Four out of the five compounds tested inhibited the capacity of *V. cholerae* to spread from the inoculation site. Next, the growth of strain C7258 was compared in a broth containing the test compounds. *V. cholerae* non-motile mutants are unaffected for growth in the broth. A compound of formula representing a quinazoline 2,4 diamine, completely abolished motility but had no effect on growth rate. Based on its high selectivity, this compound was selected for further studies.

In the *Vibrionaceae*, motility is a complex phenotype powered by sodium motive force. Expression of motility thus requires (i) the expression, secretion and assembly of the flagellum; (ii) formation of the sodium channel/flagellar motor (iii) maintenance of an inward sodium gradient by $Na^+$ efflux pumps and Na/H antiporters (iv) the coupling of sodium motive force to flagellum rotation and (v) chemotaxis (McCarter 2001). As a first approximation to target identification, the quinazoline 2,4 diamine was examined to determine if it inhibited the assembly of a polar flagellum. Transmission electron microscopy showed that this compound does not inhibit the expression, secretion and assembly of a wild type flagellum nor did it affect the level of expression of the major flagellin protein FlaA in Western blot analysis. This result indicates that this compound chemically mimics a Mot⁻ phenotype (non-motile, flagellated). This is the phenotype expected for compounds that poison the sodium channel such as phenamil, collapse the sodium gradient such as the Na ionophore monensin or mutations that inhibit flagellar function (i.e. motor, $Na^+$ gradient maintenance, energy coupling and chemotaxis).

In the cholera bacterium the motility apparatus is tightly interconnected with the expression of other phenotypes required by this pathogen to cause disease or make biofilms (Hase et al. 2001, Watnick and Kolter 1999). The effect of the quinazoline 2,4 diamine on the production of cholera toxin and the toxin-co-regulated pilus required for colonization in humans was examined. Interestingly, significantly less cholera toxin and toxin co-regulated pilus was produced by strain C7258 in the presence of this compound. In addition, the compound had a negative effect on biofilm formation when assessed at 48 h. Preliminary studies suggest that this compound paralyzes the *V. cholerae* flagellum by affecting sodium motive force.

In keeping with the present disclosure, the compounds of formula A above can be used alone or in appropriate association, and also may be used in combination with pharmaceutically acceptable carriers and other pharmaceutically active compounds. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds of formula A above alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol; isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards the use of the compounds according to this disclosure, the present method includes the administration to an animal, particularly a mammal, and more particularly a human, of a therapeutically effective amount of the compound effective in the inhibition of the motility of a motile bacteria.

The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to affect the desired response. The preferred dosage is the amount which results in maximum inhibition of the motility of a motile bacteria.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose.

The size of the dose also will be determined by the route, timing and frequency of administration as well as the existence, nature and extent of any adverse side effects that might accompany the administration of the compound and the desired physiological effect.

The attached preprint by White et al. entitled "Development of a high throughput screening assay for inhibitors of bacterial motility" and the publication by Rasmussen et al. entitled "A High Throughput Screening Assay for Inhibitors of Bacterial Motility Identifies a Novel Inhibitor of the Na$^+$-Driven Flagellar Motor and Virulence Gene Expression in *Vibrio cholarea*, Antimicrobial Agents and Chemotherapy, September 2011, p. 4134-4143, American Society for Microbiology are incorporated herein by reference.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

REFERENCES

1. Cario, E., and D. K. Podolsky. 2003. Role of Toll-like receptors in innate immunity of the intestine. In: Hecht, G. A., (Ed.) Microbial pathogenesis and the intestinal epithelial cell. ASM Press, Washington, D.C.

2. Cholera, 2009. In: Weekly epidemiological record. World Health Organization 85: 293-308, 2010.
3. Das, S., R. Saha, and I. R. Kaur. 2008. Trend of antibiotic resistance of *Vibrio cholerae* strains from east Delhi. Indian. J. Med. Res. 127: 478-482.
4. Finkelstein, R. A. 1992. Cholera enterotoxin (choleragen): a historical perspective, p. 155-187. In D. Barua and W. B. Greenough (ed.), Cholera. Plenum Medical Book Company New York
5. Guerry, P. 1994. Role of flagella in *Campylobacter* pathogenesis. In: Miller, V. L., Kaper, J. B., Portnoy, D. A. Isberg, R. R. (Eds.). Molecular Genetics of bacterial pathogenesis. ASM Press, Washington, D.C.
6. Hase, C. C., N. D. Fedorova, M. Y. Galperin, and P. A. Dibrov. 2001. Sodium ion cycle in bacterial pathogens: evidence from cross-genome comparisons. Microbiol. Mol. Biol. Rev. 65: 353-370.
7. Kaper, J. B., G. Morris Jr., and M. M. Levine. 1995. Cholera. Clin. Microbiol. Rev. 8: 48-86.
8. Kojima, S., K. Yamamoto, I. Kawagishi and M. Homma. 1999. The flagellar motor of *Vibrio cholerae* is driven by a Na+ motive force. J. Bacteriol. 181: 1927-1930.
9. Lee, S. H., S. M. Butler and A. Camilli. 2001. Selection for in vivo regulators of bacterial virulence. Proc. Natl. Acad. Sci. USA 98: 6889-6894.
10. Malapaka, R. R., A. A. Barrese III, and B. C. Tripp. 2007. High-throughput screening for antimicrobial compounds using a 96-well format bacterial motility absorbance assay. J. Biomol. Screening 12: 849-854.
11. McCarter, L. L. 2001. Polar flagellar motility of the *Vibrionaceae*. Microbiol. Molec. Biol. Reviews 65: 445-462.
12. McCormick, B. A. 2003. *Salmonella* spp.: masters of inflammation. In: Hecht, G. A., (Ed.) Microbial pathogenesis and the intestinal epithelial cell. ASM Press, Washington, D.C.
13. Mwansa, J. C., J. Mwaba, C. Lukwesa, N. A. Bhuiyan, M. Ansaruzzaman, T. Ramamurthy, M. Alam, and G. Balakrish Nair. 2007. Multiple antibiotic-resistant *Vibrio cholerae* O1 biotype E1 Tor strains emerge during cholera outbreaks in Zambia. Epidemiol. Infect. 135: 847-853.
14. Okeke, I. N., O. A. Aboderin, D. K. Byarugaba, K. K. Ojo, and J. A. Opiuntan. 2007. Growing problem of multidrug-resistant enteric pathogens in Africa. Emerg. Infect. Dis. 13: 1640-1646.
15. Roychowdhury, A., A. Pan, D. Dutta, A. K. Mukhopadhyay, T. Ramamurthy, R. K. Nandy, S. K. Bhattacharya, M. K. Bhattacharya. 2008. Emergence of tetracycline-resistant *Vibrio cholerae* O1 serotype Inaba, in Kolkata, India. Jpn. J. Infect. Dis. 61: 128-129.
16. Silva, A. J. Leitch, G. J., Camilli, A. and J. A. Benitez. 2006. Contribution of hemagglutinin/protease and motility to the pathogenesis of E1 Tor biotype cholera. Infect. Immun. 74: 2072-2079.
17. Watnick, P. I. and R. Kolter. 1999. Steps in the development of a *Vibrio cholerae* El Tor biofilm. Mol. Microbiol. 34: 586-595.

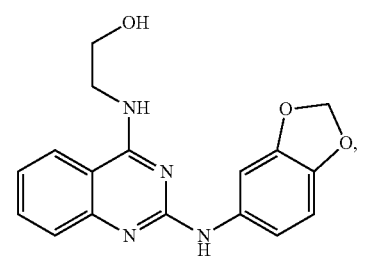
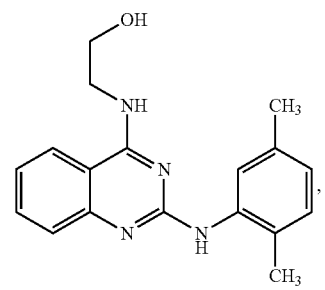 [SMILES: Cc1ccc(C)c(Nc2nc(NCCO)c3ccccc3n2)c1]
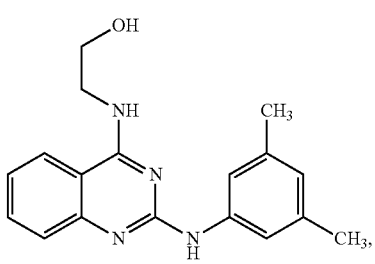
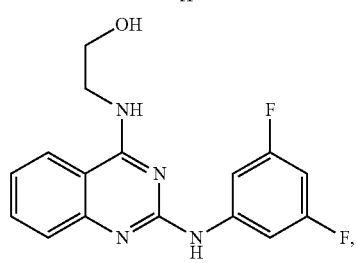
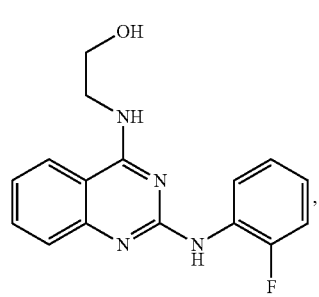
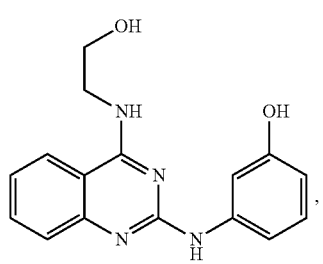
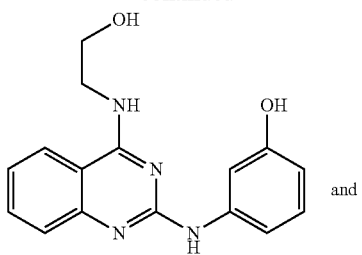
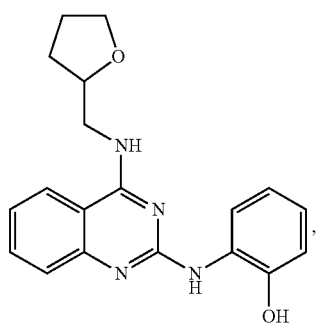
and pharmaceutically acceptable salt thereof, solvate thereof, prodrug thereof and mixtures thereof.
4. The method according to claim 1 wherein said compound is
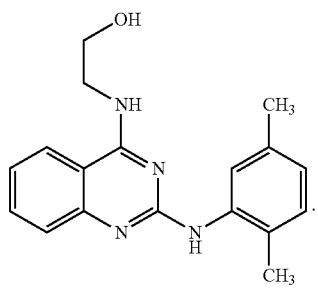
5. The method according to claim 2 wherein said compound is
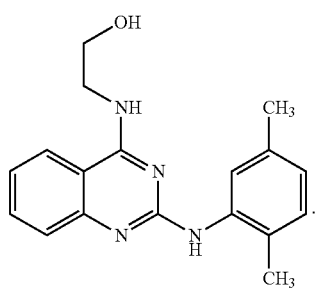 [SMILES: Cc1ccc(C)c(Nc2nc(NCCO)c3ccccc3n2)c1]

6. The method according to claim 3 wherein said compound is
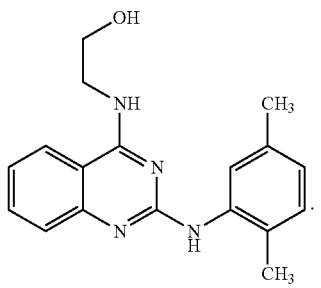 [SMILES: Cc1ccc(C)c(Nc2nc(NCCO)c3ccccc3n2)c1]

What is claimed is:
1. A method for inhibiting motility of a *Vibrio cholerae* which comprises contacting the *Vibrio cholerae* with an effective amount of a compound selected from the group consisting of at least one compound selected from the group consisting of at least one compound represented by the following formulae:

-continued

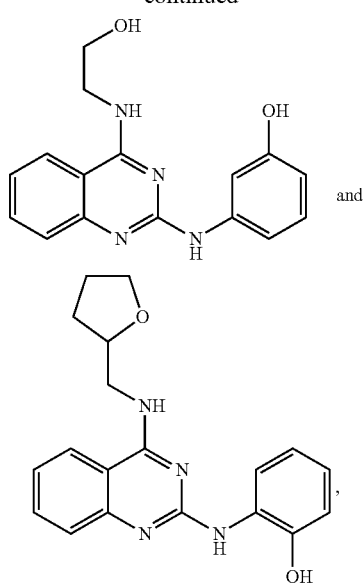

and pharmaceutically acceptable salt thereof, solvate thereof, prodrug thereof and mixtures thereof.

2. A method for treating a patient by inhibiting motility of *Vibrio cholerae* in a patient exposed to the *Vibrio cholerae* which comprises administering to the patient an effective amount of a compound selected from the group consisting of at least one compound represented by the following formulae:

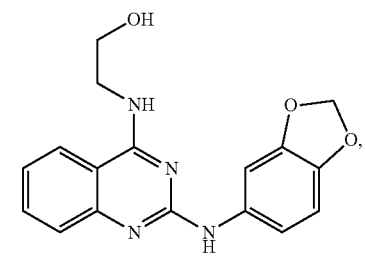

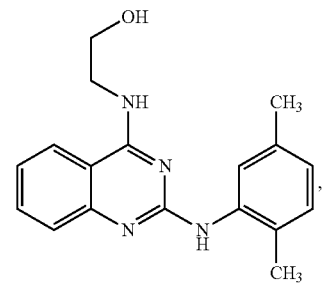

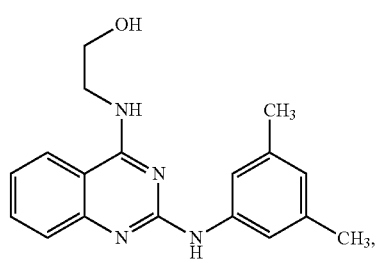

-continued

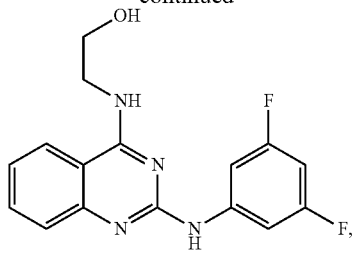

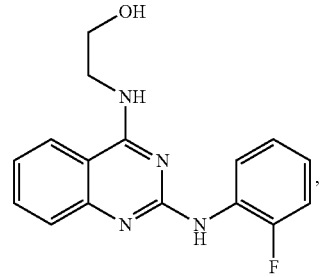

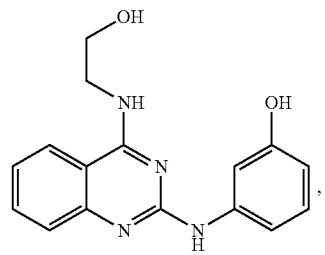

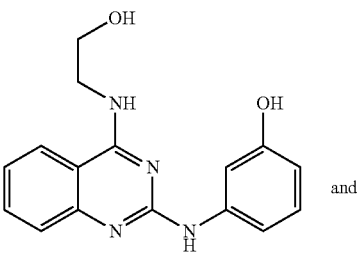

and

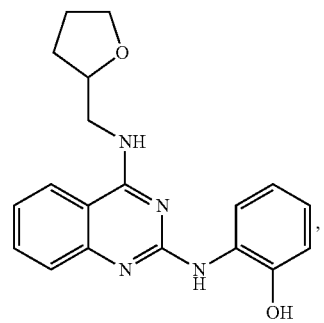

and pharmaceutically acceptable salt thereof, solvate thereof, prodrug thereof and mixtures thereof.

3. A method for the prophylaxis treatment of a cholera outbreak due to the *Vibrio cholerae* by administering to a patient in danger of exposure to the *Vibrio cholerae* at least one compound selected from the group consisting of at least one compound represented by the following formulae: